United States Patent
Lane et al.

(10) Patent No.: US 10,076,601 B2
(45) Date of Patent: Sep. 18, 2018

(54) IMPLANTED TUBE AND EXTERNAL INTERFACE FOR SALINE OR DRUG DELIVERY TO THE PARANASAL SINUSES

(71) Applicant: THE JOHNS HOPKINS UNIVERSITY, Baltimore, MD (US)

(72) Inventors: Andrew P. Lane, Baltimore, MD (US); Anastasia Victoria Borok Russell, Baltimore, MD (US); Creighton Ralph Petty, Baltimore, MD (US); Lauren Kraiter, Baltimore, MD (US); Marton Varady, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 801 days.

(21) Appl. No.: 14/383,933

(22) PCT Filed: Mar. 11, 2013

(86) PCT No.: PCT/US2013/030150
§ 371 (c)(1),
(2) Date: Sep. 9, 2014

(87) PCT Pub. No.: WO2013/134758
PCT Pub. Date: Sep. 12, 2013

(65) Prior Publication Data
US 2015/0088098 A1    Mar. 26, 2015

Related U.S. Application Data

(60) Provisional application No. 61/608,916, filed on Mar. 9, 2012, provisional application No. 61/621,155, filed on Apr. 6, 2012.

(51) Int. Cl.
*A61M 31/00* (2006.01)
*A61M 3/02* (2006.01)
*A61M 39/10* (2006.01)

(52) U.S. Cl.
CPC .......... *A61M 3/0279* (2013.01); *A61M 31/00* (2013.01); *A61M 39/10* (2013.01); *A61M 2210/0681* (2013.01)

(58) Field of Classification Search
CPC ................ A61K 9/0043; A61M 31/00; A61M 2210/0681; A61M 3/0279; A61M 16/0666; A61F 2/186
See application file for complete search history.

(56) References Cited

U.S. PATENT DOCUMENTS 5,507,731 A * 4/1996 Hernandez ............ A61M 25/00
604/264
7,762,253 B2 7/2010 Acker et al.
(Continued)

FOREIGN PATENT DOCUMENTS

WO    2012/020004 A1    2/2012

*Primary Examiner* — Rebecca E Eisenberg
(74) *Attorney, Agent, or Firm* — Johns Hopkins Technology Ventures

(57) ABSTRACT

An embodiment in accordance with the present invention provides an implanted catheter and an external device that the patient uses to inject a therapeutic into the implanted tube. The implanted catheter can be equipped with a fixation mechanism that secures the catheter in place and eases physician insertion and removal. The fixation mechanism can include shape memory arms having silicone tips or can be a second catheter branch configured to hold the device in the user's sinus cavity. The catheter can also include numerous exit holes to prevent obstruction and deliver the therapeutic. An interface between the implanted catheter and the external device is incorporated, to ensure a reliable seal for medication passage. A method and device for delivery of the catheter to the correct position can also be included.

9 Claims, 13 Drawing Sheets

(56) References Cited

U.S. PATENT DOCUMENTS

| | | |
|---|---|---|
| 2004/0035430 A1 | 2/2004 | Wright |
| 2008/0183128 A1* | 7/2008 | Morriss ............... A61M 3/0283 604/35 |
| 2009/0017090 A1 | 1/2009 | Arensdorf et al. |
| 2012/0000460 A1 | 1/2012 | Flickinger |

* cited by examiner

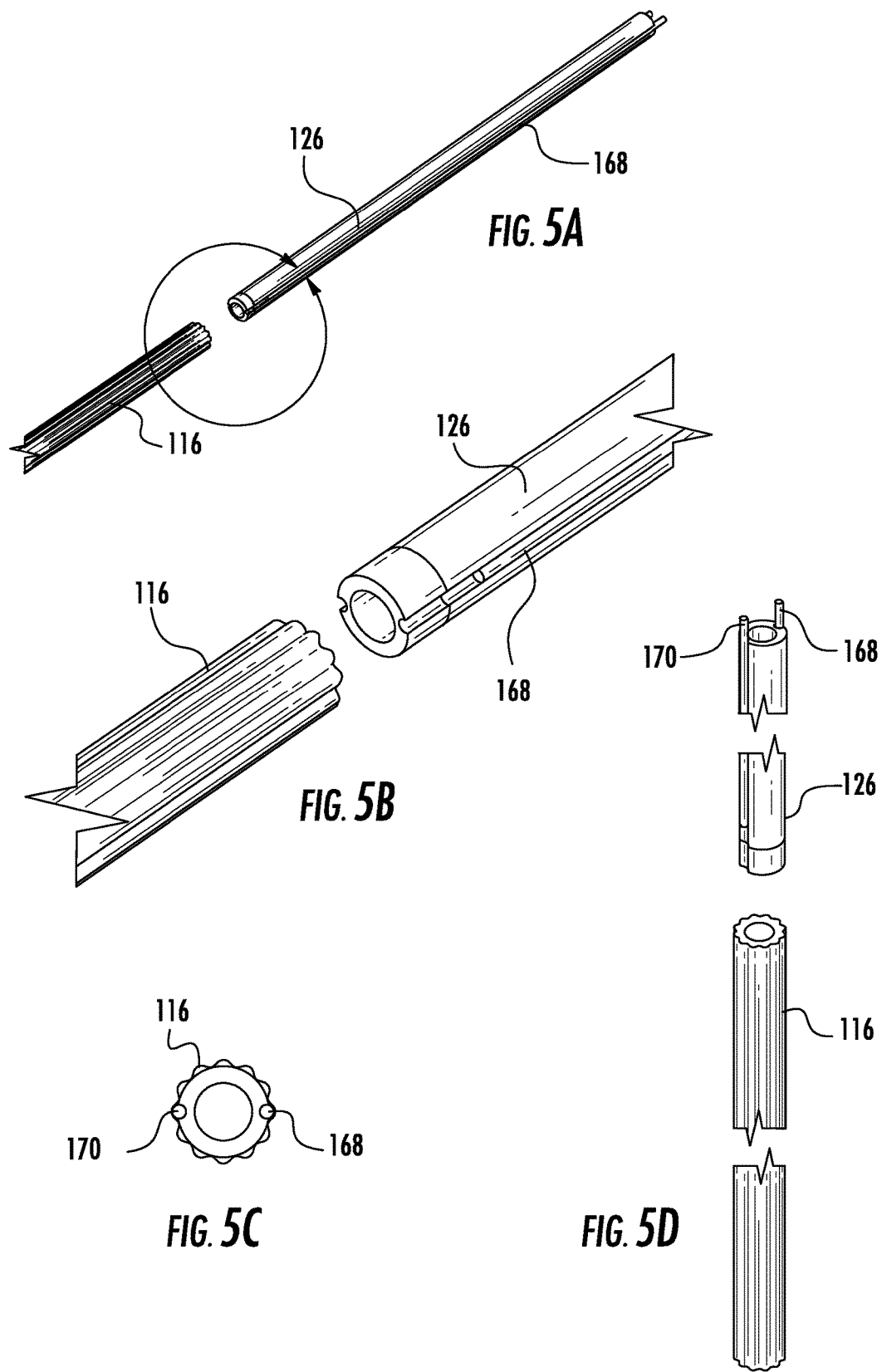

IMPLANTED TUBE AND EXTERNAL INTERFACE FOR SALINE OR DRUG DELIVERY TO THE PARANASAL SINUSES

CROSS-REFERENCE TO RELATED APPLICATIONS

This application is a 35 U.S.C. § 371 U.S. national entry of International Application PCT/US2013/030150 having an international filing date of Mar. 11, 2013, which claims the benefit of U.S. Provisional Application No. 61/608,916, filed on Mar. 9, 2013, and U.S. Provisional Application No. 61/621,155, filed on Apr. 6, 2012 the content of each of the aforementioned applications is herein incorporated by reference in their entirety.

FIELD OF THE INVENTION

The present invention relates generally to treatment of chronic sinusitis. More particularly, the present invention relates to an implantable device with an external drug delivery component for treatment of chronic sinusitis.

BACKGROUND OF THE INVENTION

Between three and ten million people in the United States suffer from chronic sinusitis. Chronic sinusitis is the persistent inflammation of the paranasal sinus lining. The inflammation can obstruct normal mucosal flow and can lead to infection, nasal congestion, facial pressure, headache, fever, fatigue, and other symptoms that severely impair quality of life. Though topical steroid or antibiotic delivery and saline irrigation are known to improve the symptoms of chronic sinusitis, current delivery methods largely fail to reach affected areas.

It would therefore be advantageous to provide an implant and a corresponding external drug delivery component to deliver medication directly to the sinuses.

SUMMARY OF THE INVENTION

The foregoing needs are met, to a great extent, by the present invention, wherein in one aspect a system for delivery of a therapeutic substance to a user's sinus cavity includes an implantable tube having a proximal end, a distal end, and a lumen extending therethrough. The implantable tube is configured to extend into the user's sinus cavity via the user's nasal passage. The implantable tube is also configured to transmit the therapeutic substance to the user's sinus cavity. An anchor segment is coupled to the implantable tube configured to secure the implantable tube in the sinus cavity. An external delivery component has a reservoir coupled to a delivery tube configured to extend into the user's nasal passage. The external delivery component is configured to deliver the therapeutic substance through the delivery tube and into the implantable tube for delivery into the user's sinus cavity. The device also includes an interface between the implantable tube and the external delivery component configured to guide and lock the implantable tube to the external delivery component.

In accordance with an aspect of the present invention, the interface for the system for delivery of the therapeutic substance to the user's sinus cavity includes a magnetic interface. The anchor segment further includes a curved configuration for securing the implantable tube within a maxillary sinus cavity of the user. The anchor segment can also take the form of a shape memory wire. The implantable tube is disposed in an ethmoidal sinus of the user. Additionally, the device can include a delivery sheath configured to deliver the implantable tube to the user's sinus cavity. The delivery sheath is further configured to compress the anchor segment until the implantable tube is in a desired location in the user's sinus cavity. The implantable tube further includes perforations to allow the therapeutic substance to transmit into the user's sinus cavity. The lumen of the implantable tube is in fluid communication with a lumen of the delivery tube. The external delivery component also includes a mechanism configured to apply force to separate the interface between the external delivery device and the implantable tube.

In accordance with another aspect of the present invention, a system for delivery of a therapeutic substance to a user's sinus cavity includes an implantable tube having a first branch configured to extend into an ethmoidal sinus cavity of the user. The implantable tube also has a second branch configured to extend into a maxillary sinus cavity of the user. The first and second branches of the implantable tube are further configured to transmit the therapeutic substance to the user's sinus cavity. An external delivery component has a reservoir coupled to a delivery tube configured to extend into the user's nasal passage. The external delivery component is configured to deliver the therapeutic substance through the delivery tube and into the implantable tube for delivery into the user's sinus cavity. The device also includes an interface between the implantable tube and the external delivery component configured to guide and lock the implantable tube to the external delivery component.

In accordance with another aspect of the present invention, the interface takes the form of a magnetic interface. The first and second branches of the implantable tube each comprise a lumen extending therethrough. The implantable tube also includes a proximal end segment having a lumen therethrough. The lumen of the proximal end is configured to be in fluid communication with the lumen of the first branch and the lumen of the second branch. A delivery sheath is configured to deliver the implantable tube to the user's sinus cavity. The delivery sheath is further configured to compress the second branch until the implantable tube is in a desired location in the user's sinus cavity. The implantable tube further includes perforations to allow the therapeutic substance to transmit into the user's sinus cavity. The lumen of the proximal end of implantable tube is in fluid communication with a lumen of the delivery tube. The external delivery component includes a mechanism configured to apply force to separate the interface between the external delivery device and the implantable tube. The implantable tube is formed from a medical grade silicone. In addition, the implantable tube is formed from a material with a durometer of approximately 55D.

In accordance with yet another aspect of the present invention a method for delivery of a therapeutic substance to a user's sinus cavity includes delivery of an implantable tube to the user's sinus cavity using a delivery catheter and deploying the implantable tube into the user's sinus cavity. The method also includes coupling the implantable tube to an external delivery component filled with the therapeutic substance and locking the implantable tube to the external delivery component. Additionally, the method includes dispensing the therapeutic agent from the external delivery device through the implantable tube to the user's sinus cavity and uncoupling the external delivery device from the implantable tube.

BRIEF DESCRIPTION OF THE DRAWINGS

FIGS. 5A-D illustrate side and perspective views of the interface design in accordance with an embodiment of the invention.

DETAILED DESCRIPTION

Figure 1:
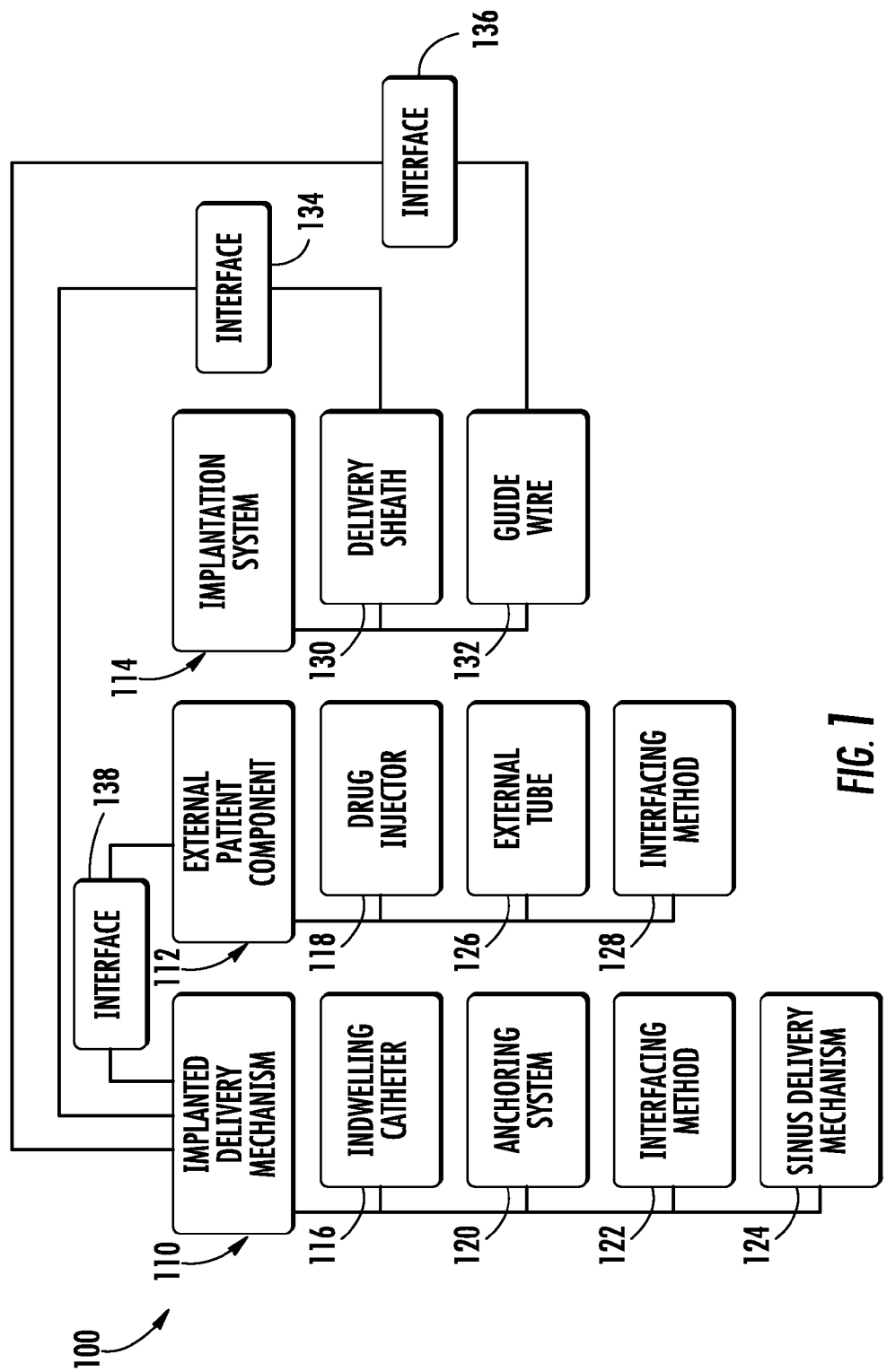
FIG. 1 illustrates a diagram of the system for the implanted delivery mechanism, external drug delivery component and implantation, in accordance with an embodiment of this invention.
Figure 2:
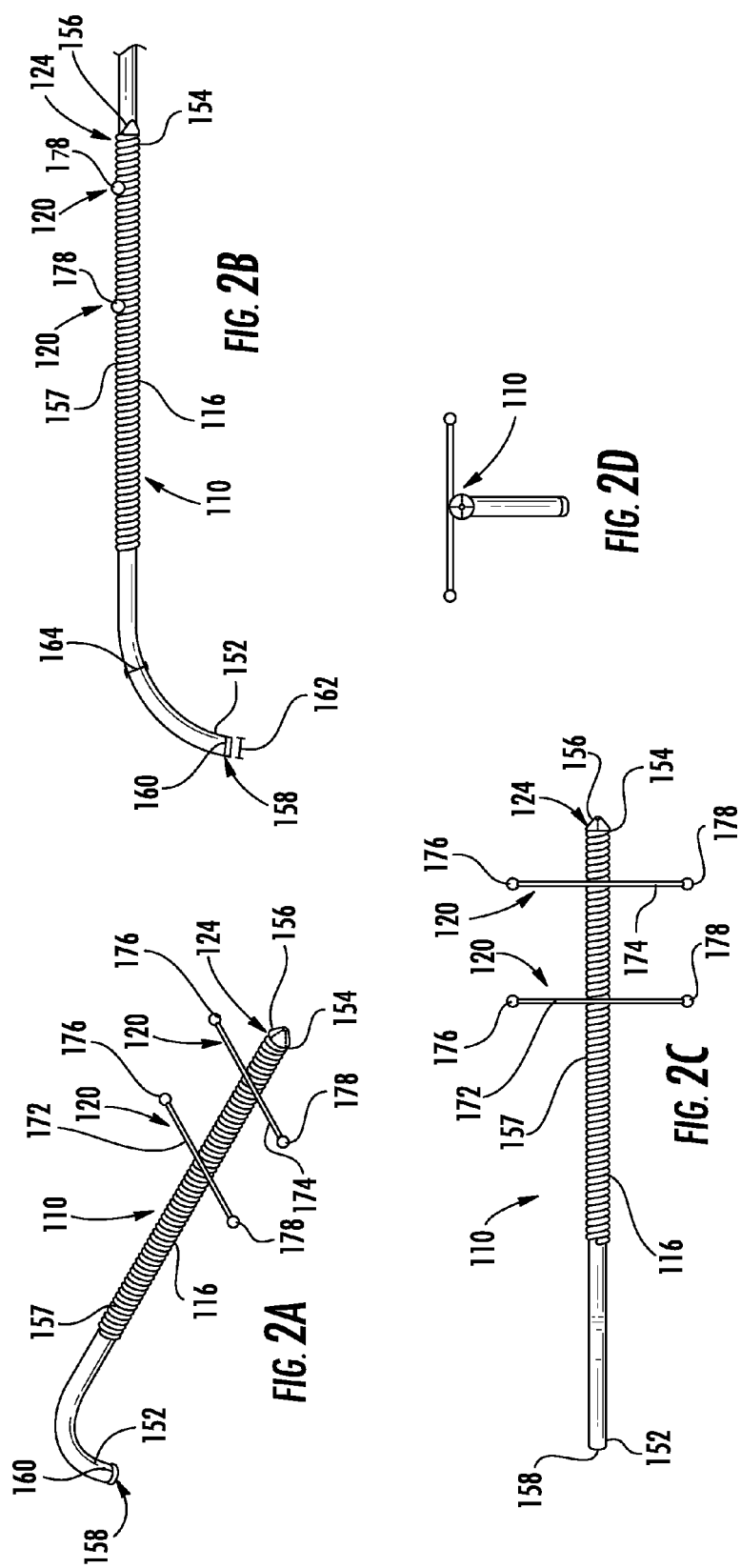
FIGS. 2A-2D illustrate views of the implanted delivery mechanism in accordance with an embodiment of the present invention.

The invention will now be described with reference to the drawing figures, in which like reference numerals refer to like parts throughout. An embodiment in accordance with the present invention provides a small implanted catheter and an external device that the patient users to inject saline or a drug solution into the implanted tube. The distal end of the catheter is disposed in the sinus cavity such that a drug or saline can be delivered directly to the sinuses. The implanted catheter can be equipped with a fixation mechanism that secures the catheter in place and eases physician insertion and removal. The fixation mechanism can include shape memory arms having silicone tips. The catheter can also include a textured surface and numerous exit holes to prevent obstruction as well as facilitate drug delivery. An interface between the implanted catheter and the external device is incorporated, to ensure a reliable seal for medication passage. A mechanism of disconnecting the interface between the implanted catheter and the external device, such as to reduce force exerted on the implanted catheter, can also be included. A method and device for delivery and removal of the catheter to/from the correct position can also be included.

FIG. 1 illustrates a diagram of the system 100 for the implanted delivery mechanism 110, external drug delivery component 112 and implantation 114, in accordance with an embodiment of this invention. The diagram of FIG. 1 shows that the implanted delivery mechanism 110 includes an indwelling catheter portion 116 of the device that remains in the nasal passage and sinus cavity. It is initially implanted by the physician during surgery or during an office visit before or after a surgical procedure. The external patient component 112 is a drug injector reservoir 118 shaped similar to conventional spray bottles to which the patient is accustomed. The external patient component 112 will be used by the patient on a daily basis. The patient will insert it into the nostril and it will interface with the implanted delivery mechanism 110. The patient will physically operate the external patient component 112 to pass drug into the implanted delivery mechanism 110. The implantation system 114 consists of accessories that the physician will use to insert and remove the implanted delivery mechanism component. It can be used following surgery or during an office visit.

More particularly with respect to the system diagram illustrated in FIG. 1, the implanted delivery mechanism 110 consists of an indwelling catheter 116, anchoring system 120, interfacing method 122, and sinus delivery mechanism 124. The structure of the components shown in FIG. 1 will be described in further detail with respect to the additional reference figures herein. However, briefly, the indwelling catheter 116 is a tube-like device that is inserted into the nasal passage and sinus. It has an inner lumen through which the drug passes to travel from the proximal end to the distal end. The sinus delivery mechanism 124 is the superior end of the indwelling catheter. It has numerous perforations concentrated at and near the proximal tip. It may have a textured surface of "grooves" or "divots" with the perforations located at the deepest portion of the groove/indentation. The perforations are the exit site for drug delivery into the sinus. The textured surface is designed to prevent inflamed tissue or mucus from occluding the perforations.

The anchoring system is intended to fixate the device within the nasal passage. It is designed such that it can be compressed during initial implantation, then spring out to hold the implanted delivery mechanism in place. The anchoring system 120 design consists of two arms situated perpendicular to the long axis of the indwelling catheter 116. The arms include a larger surface area component at the distal tip to avoid tissue puncture and enhance traction and stability. The interfacing method 122 on the implanted delivery mechanism 110 is designed to guide the external patient component such that it can interface with the implanted delivery mechanism 110. It is also designed to prevent the leakage of drug fluid as it is passed form the external patient component to the implanted delivery mechanism.

Additionally, while the structure of the external patient component subsystems 112 will be described in further detail below, the external patient component subsystems 112 include a drug injector 118, external tube 126, and interfacing method 128. The drug injector 118 includes a small reservoir of drug and has a mechanism to ensure the appropriate dosage for delivery into the sinuses. The patient may either fill the drug injector prior to use of the device, or pump or squeeze the device to dispense the appropriate amount of drug is released. The external tube 126 is connected to the drug injector 118. It is the portion of the external patient component 112 that the patient inserts into the inferior portion of the nostril. The external tube 126 provides a lumen through which drug flows from the drug injector up to the implanted delivery mechanism. The interfacing method 128 is designed to be guided or attracted to the interfacing method 122 of the implanted delivery mechanism 110. It ensures alignment with the implanted delivery mechanism 110 and also prevents leakage of drug fluid during passage between the external patient component 112 and implanted delivery mechanism 110. The interfacing method 128 may also include a disconnection mechanism. The disconnection portion is designed to detach the connected magnets with minimal force applied to the anchoring mechanism of the implanted delivery mechanism 110. The disconnection portion is operated from the external patient component. In one embodiment of the invention, the disconnection portion, deploys superiorly and can exert a repelling force against the interfacing method of the implanted delivery mechanism 110.

Also, as illustrated in FIG. 1, the implantation system 114 consists of a delivery sheath 130 and guide wire 132. The guide wire 132 may be used for the physician to obtain access to the desired site of placement in the sinus. For initial placement of the device, the physician will navigate the guide wire 132 into the cavity using endoscopic guidance. For replacement of an existing implant, the physician may insert the guide wire 132 through the lumen of the existing implant before removing it. In either case, the guide wire will be held in place while the implanted delivery mechanism 110 is passed over it and then removed. The delivery sheath 130 will be used when implanting the implanted delivery mechanism 110. The delivery sheath 130 will completely cover at least the anchoring component 120 of the implanted delivery mechanism 110 and apply pressure to constrain the anchoring component 120. Alternatively, the physician may insert the implanted catheter with sheath covering without the use of the guidewire. This could be achieved using other office tools such as forceps. In either case, once the implanted delivery mechanism 110 is in place, the delivery sheath 130 will be retracted out of the nasal passage such that the anchoring component is allowed to spring radially outward.

As is apparent from the preceding description of FIG. 1, the implanted delivery mechanism 110, external patient component 112, and implantation system 114 are all interfaced to provide treatment to the patient. One interface 134 is between the delivery sheath 130 and the implanted delivery mechanism 110. As described above, the implanted delivery mechanism 110 must fit easily into the delivery sheath 130. The delivery sheath 130 applies pressure to the anchoring mechanism 120, which allows for the implanted delivery mechanism 110 to be inserted into the ideal location between the nasal passage and the sinus cavity. Another interface 136 is between the implanted delivery mechanism 110 and the guide wire 132. The implanted delivery mechanism 110 can be back-loaded over the guide wire 132. The guide wire 132 passes through the lumen of the indwelling catheter 110. Another interface 138 is between the implanted delivery mechanism 110 and the external patient component 112. The implanted delivery mechanism 110 and external patient component 112 temporarily lock together during drug delivery. The external patient component 112 has a mechanism which can apply a force to separate the two.

In more detail, the external patient component 112 includes the drug injector 118, external tube 126, and interfacing method 128 in accordance with the embodiment of the invention. The drug injector 118 can take the form of a syringe, but alternately, can take the form of a pump or spray bottle or other convenient means of administering the drug or saline. The external patient component 112 is designed to allow the patient to easily attach the external medication delivery tube 126 to their implanted drug delivery system 110. The external medication delivery tube 126 can be formed from medical grade silicone tubing for biocompatibility and comfort or any other suitable tubing. Because the implanted system 110 is designed to be covert, the patient needs to be able to safely and effectively interface with something that they cannot easily see. The distal end of the medication delivery tube 126 is designed to be compatible with the drug injector 118 (syringe or nasal sprayer) that will deliver the drug into the external medication delivery tube 126. This can be accomplished for example, through using an airtight sealing mechanism, a screwing mechanism, or other suitable mechanism for connecting the drug injector 118 and the delivery tube 126.

More particularly, the proximal end of the delivery tube will house the external component of the interface between the delivery tube 126 and the implanted drug delivery system 110. The internal component of the interface can be positioned at the distal end of the implanted system. A proposed mechanism for interfacing the internal implanted system 110 and the external patient component is magnetic. However, any other suitable means of interfacing the two components could be used. The magnet on the delivery tube 126 can serve as the connection point between itself and the indwelling catheter 116 of the internal delivery mechanism 110. Additionally, the outer diameter of this magnet can preferably be equal to the outer diameter of delivery tube 126, making its connection seamless. This will ideally prevent/limit possible irritation to the sinus anatomy. The magnets on each end will secure the two tubes to each other, allowing for the delivery of the drug. The magnet can take any suitable form, but preferably the magnets used for both the internal and external components are titanium coated for biocompatibility and durability.

Figure 3:
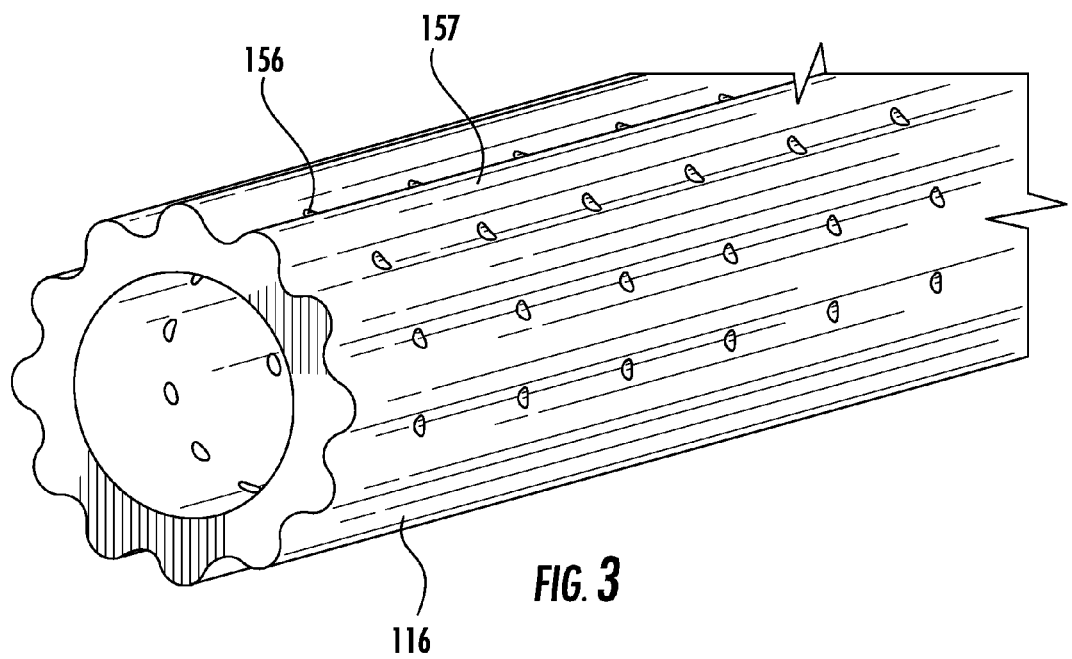
FIG. 3 illustrates a perspective view of the implanted delivery mechanism in accordance with an embodiment of the present invention.

FIGS. 2A-2D illustrate the implanted delivery mechanism 110 in accordance with an embodiment of the present invention. As described above, the implanted delivery mechanism 110 includes an indwelling catheter 116, an anchoring system 120, an interfacing method, 122, and a sinus delivery mechanism 124. The indwelling catheter 116 can take the form of a perforated delivery tube having a lumen extending therethrough. The indwelling catheter 116 can be formed from any suitable material, but preferably the catheter 116 is formed from medical grade silicone or polyurethane. A distal end 152 of the indwelling catheter can connect with the external patient component 112. A proximal end 154 can be located within the specified sinus of the patient. The indwelling catheter 116 includes small perforations 156 along the length of the catheter 116, in order to facilitate the spread of the drug throughout the sinus cavity. The catheter 116 can have lengthwise or crosswise ridges 157, as illustrated in FIG. 3, to (a) prevent unnecessary movement within the nasal passageways and (b) to help drug seep through the perforations despite possible encroaching diseased tissue or the presence of mucus. Alternately, the catheter 116 need not have any ridges at all. The distal end 152 of the catheter 116 will house the interface component 158 intended to interface with the distal end of the external patient component.

The interfacing component 158 can be located on the distal end 152 of the catheter 116. The proposed mechanism for interfacing is magnetic. The magnet 160 on the indwelling catheter 116 serves as the connection point between itself and the external patient component 112. Additionally, the outer diameter 162 of this magnet 160 can be equal to the outer diameter 164 of the perforated delivery tube, making its connection seamless. This can prevent/limit possible irritation to the sinus anatomy. The magnets on each end will secure the two tubes to each other, allowing for the delivery of the drug. The magnet can take any suitable form, but preferably the magnets used for both the internal and external components are titanium coated for biocompatibility.

The sinus delivery mechanism 124 is located on the proximal end 154 of the indwelling catheter 116. This, in essence, is the portion of the indwelling catheter 116 that is located deepest within the sinus cavity. The sinus delivery mechanism 124 can be formed from any suitable material, but preferably the mechanism 124 is formed from medical grade silicone or polyurethane. It is designed such that the injected drug can reach as much surface area of the sinus as possible. The indwelling catheter 116 can have ridges designed to prevent occlusion of the drug exit holes or perforations 156 from inflamed tissue or mucus. A large portion of the exit holes may also be located inside sinus passages or a cavity. The ridges can be helical or longitudinal, as illustrated in FIGS. 2A-D and 3.

Figure 4A:
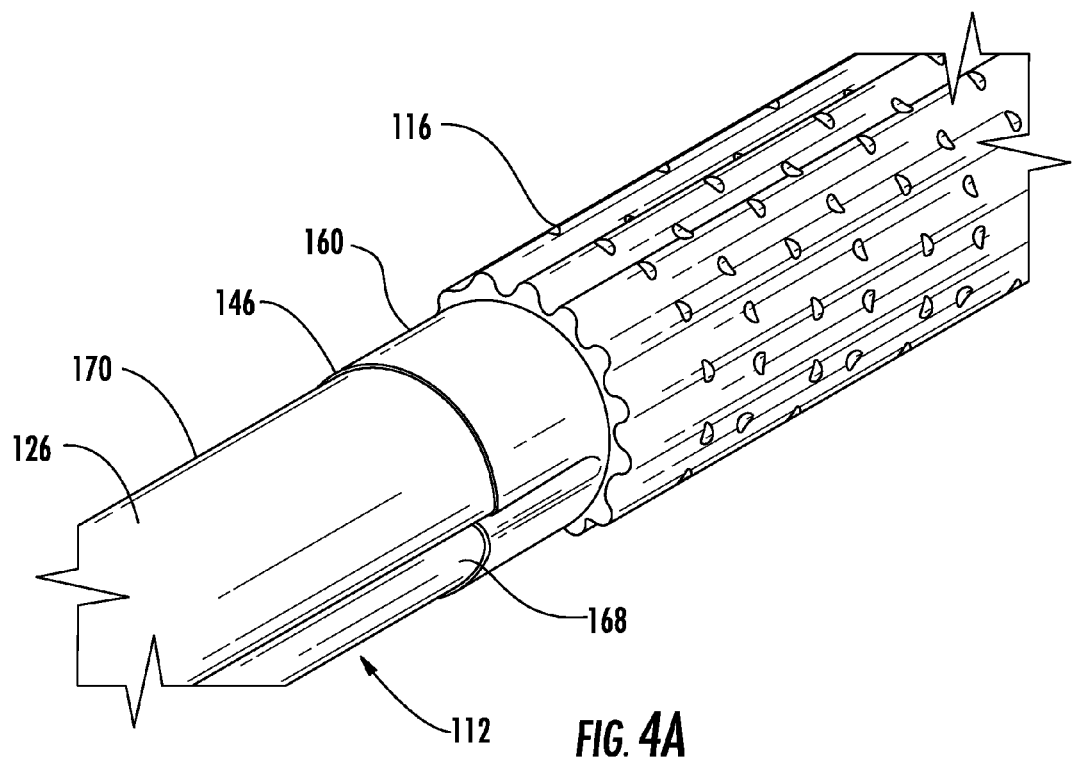
FIGS. 4A and 4B illustrate side views of the magnetic interface in accordance with an embodiment of this invention.
Figure 4B:
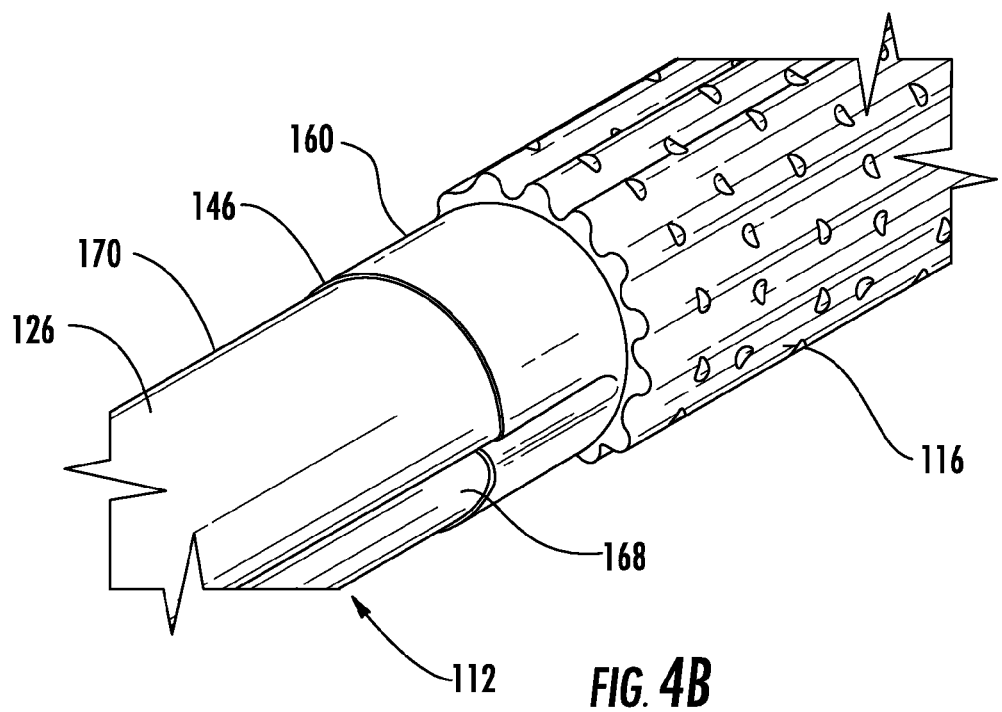
Figure 6:
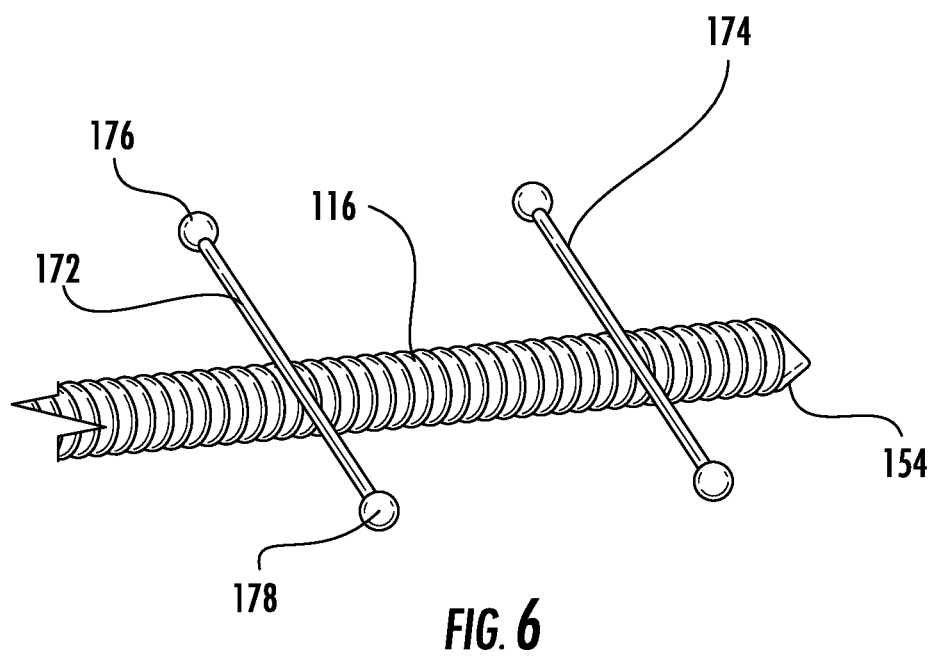
FIG. 6 illustrates a perspective view of the implanted delivery mechanism in accordance with an embodiment of the invention.

FIGS. 4A and 4B illustrate the magnetic interface in accordance with an embodiment of this invention. The magnetic interface can be separated using a "plunger" design that avoids placing excess force on the implanted component during disconnection and therefore lowers the risk of dislodgement. The plunger disconnection design consists of two rods 168, 170 running parallel to a longitudinal axis "A" of the external delivery tube 126, through the outer circumference of the external interface magnet 146. The two rods 168, 170 are deployed superiorly following drug injection and exert a force upon the implanted interface magnet 160. Because the implanted interface is fixed in place, the applied force propels the external component slightly inferiorly. Once the magnets 146, 160 are separated, the patient can easily remove the external component 112. A major advantage of this iteration is it could be physically triggered immediately following drug injection, so the patient does not have to remember to activate the disconnection mechanism. FIGS. 5A-D also illustrate the interface design in accordance with the invention. Alternatively, rather than the rods, a non-magnetic outer tube could encircle the length of the external tube, and then be activated to deploy superiorly so that it pushes against the implanted interface component to force the external component inferiorly (not pictured). Other disconnection mechanisms may be used, such as a sliding mechanism that exerts a shear force on the external tube (not pictured).

As illustrated in FIGS. 2A-D and FIG. 6, C-arms with soft rounded tips at the end can be configured to deploy radially from the indwelling catheter and secure the indwelling catheter by exerting a force against the surrounding tissue. An advantage is the C-arms will function in varying anatomy with different widths of passages or sinus cavities. The osteum attachment as illustrated in FIGS. 2A-D and FIG. 6 can have two wires 172, 174 attached at the proximal end 154 of the catheter 116. These wires 172, 174 can spread out after the delivery sheath (not pictured) is removed from the implanted device, thus preventing it from falling out of the sinus cavity. While the wires 172, 174 can be formed from any suitable material, preferably the wires are formed from nitinol. The wires 172, 174 can also include silicone tips 176, 178 at their ends to provide comfort to the patient. The wires on either side of the implanted device may be composed of one continuous wire that passes through the implanted device lumen. Additionally, the wires may be combined in different ways to provide fixation, such as in a 90-degree orientation relative to one another, forming a cross shape (not pictured). There may also be more than two wires used to form the fixation mechanism.

An alternative to securing the implanted catheter 116 by its proximal end 154 is to anchor it by its distal end 152. The distal end 152 could be anchored using either sutures or staples in the portion of the nose extending out of the skull, under the nasal bone and along the lateral cartilage. This would ensure that the catheter 116 does not occlude the inhalation process and it appears to be a less fragile and sensitive area of the nose.

A delivery sheath can be used to cover the implanted delivery mechanism encompassing the distal end of the perforated catheter 116 up to the proximal end of the sinus cavity delivery mechanism in order to ease the process of implantation. This delivery sheath can take the form of a flexible catheter or any other suitable sheath. The delivery sheath can have a diameter that is large enough to contain the perforated catheter as well as compress the wires 172 and 174 illustrated in FIGS. 2A-D and 6, in order to ease the delivery into the sinus passage. The sheath can then be removed after the physician has placed the catheter 116 in the desired location within the sinus passage.

Figure 7:
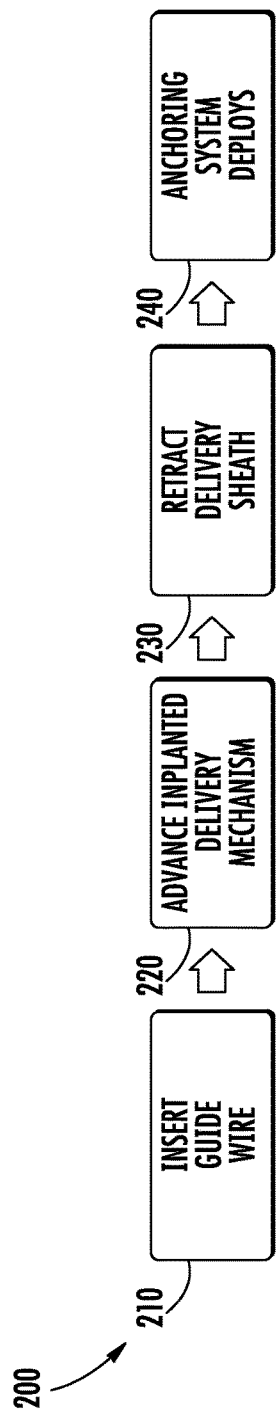
FIG. 7 illustrates a diagram showing the physician implantation process in accordance with an embodiment of the invention.

FIG. 7 illustrates the physician implantation process 200 in accordance with the invention. Step 210 includes inserting the guide wire into the patient. Step 220 includes advancing the implanted delivery mechanism including a delivery sheath surrounding the implantable catheter, and step 230 includes retracting the delivery sheath. Also, step 240 includes deploying the anchoring system.

Figure 8:
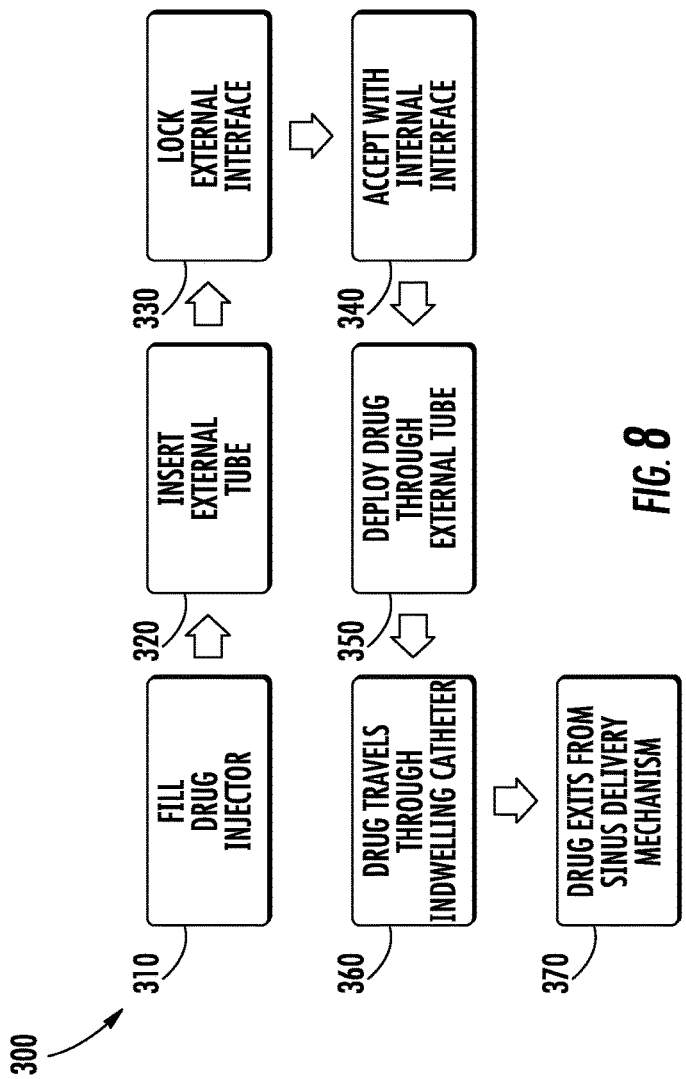
FIG. 8 illustrates a diagram showing the process of delivering medication to the sinuses in accordance with an embodiment of the invention.

FIG. 8 illustrates the drug delivery process 300 in accordance with the invention. Step 310 includes filling the drug injector and step 320 includes inserting the external tube. The external interface is locked together in step 330, and step 340 includes joining the external and internal interfaces together. Step 350 includes deploying the drug through the external tube and step 360 includes the drug travelling through the indwelling catheter. Finally, the drug exits from the sinus delivery mechanism, in step 370.

Figure 9:
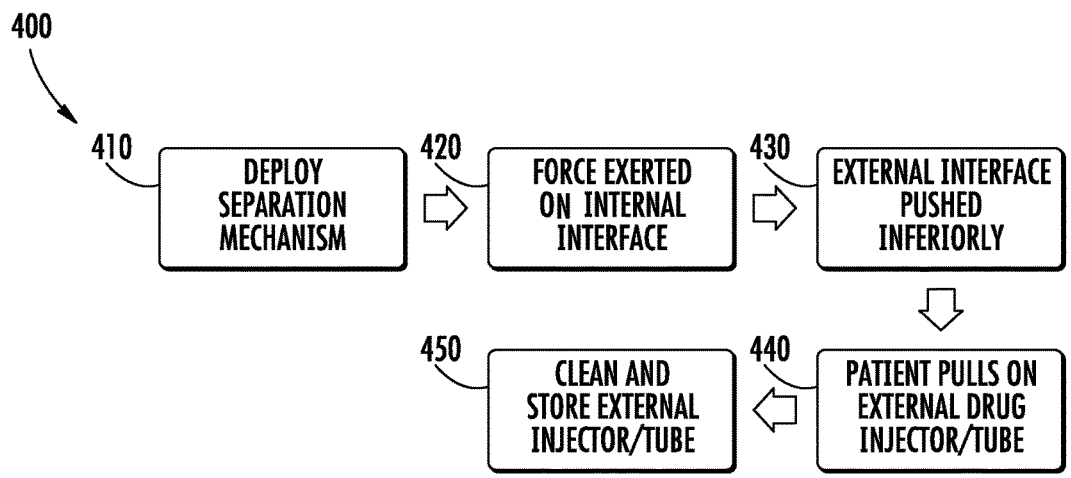
FIG. 9 illustrates a diagram showing the device removal process in accordance with an embodiment of the invention.

FIG. 9 illustrates the process of removing the external component from the nose once drug delivery is completed 400, in accordance with the invention. Step 410 includes deploying the separation mechanism, and step 420 includes exerting force on the internal interface. Step 430 includes the external interface being pushed inferiorly, and step 440 includes the patient pulling on the external drug injector/tube. Additionally, step 450 includes cleaning and storing the external injector and tube.

Figure 10A:
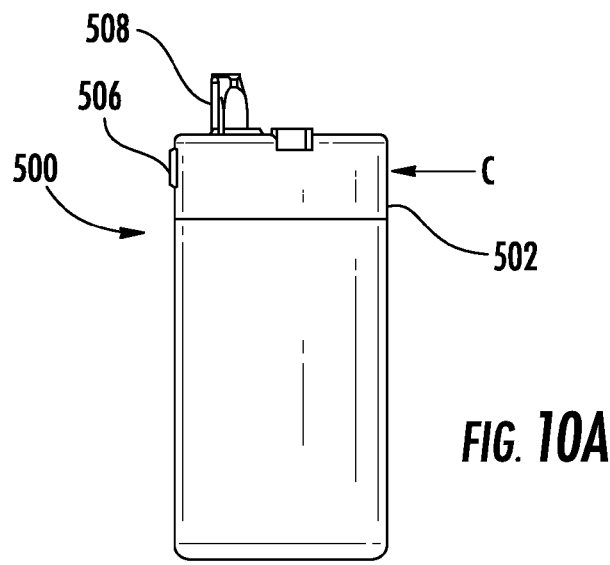
FIGS. 10A-10C illustrate an embodiment of the external delivery device component, which consists of a pumping mechanism, fluid release button, external magnetic interface, and a decoupling mechanism for separating the external and internal components.
Figure 10B:
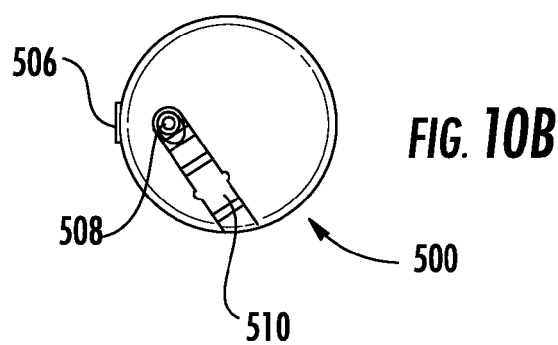
Figure 10C:
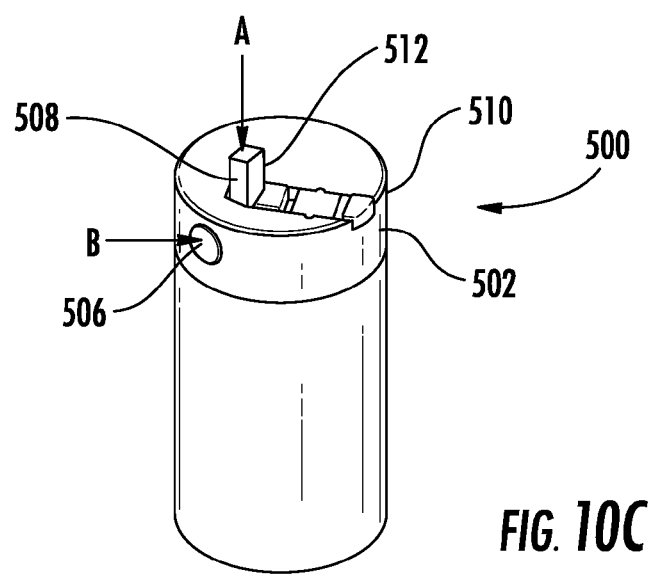

FIGS. 10A-10C illustrate an embodiment of the external component of the device. The drug reservoir 500 has a lid 502 that can be screwed on and off for refilling it with drug or saline. There is a pumping mechanism (not pictured) that the user operates to build pressure within the reservoir chamber. A fluid release button 506 releases pressure on the external tube 508 to allow the saline or drug to exit. A horizontally sliding mechanism 510 can be operated by the user to shift the external tube 508 horizontally such that it applies a shear force at the magnetic interface 512 to disengage the magnetic connection.

Figures 11A, 11B:
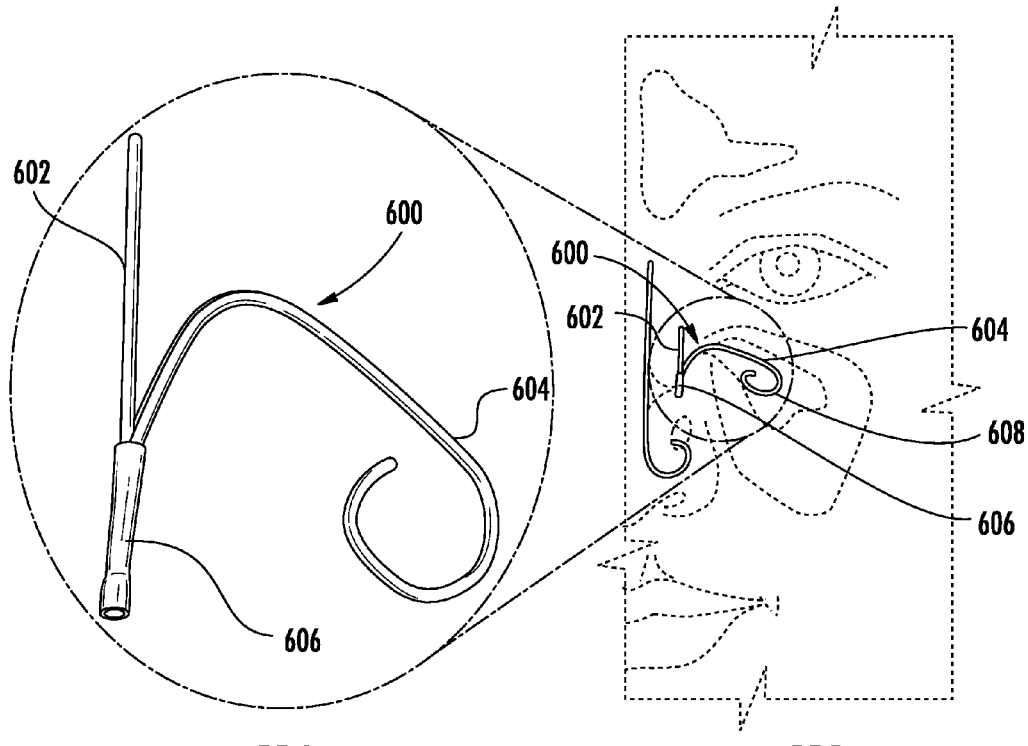
FIGS. 11A-11C illustrate an embodiment of a catheter for delivery of therapeutic substances to the sinuses.
Figure 11C:
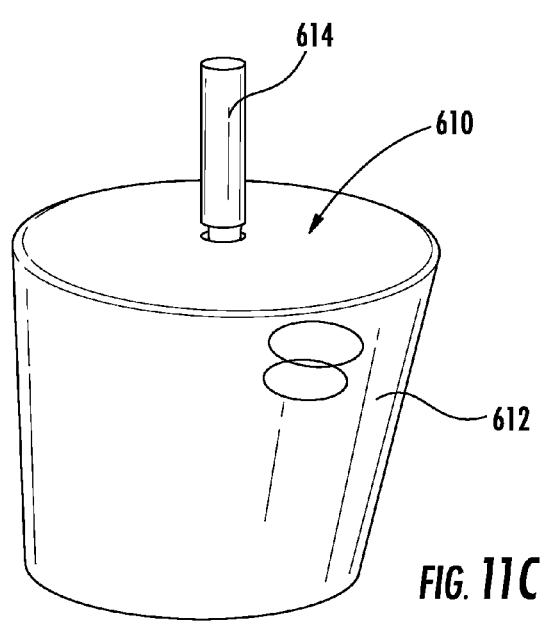

FIGS. 11A-11C illustrate an embodiment of a catheter for delivery of therapeutic substances to the sinuses. As illustrated in FIG. 11A the catheter 600 includes a first branch 602 and a second branch 604. The first branch 602 of the catheter 600 is configured to extend into an ethmoid sinus of the patient. The second branch 604 of the catheter 600 is configured to extend into a maxillary sinus of the patient. Both the first and second branches 602, 604 of the catheter include small perforations that distribute the therapeutic substance evenly within the ethmoid and maxillary sinus cavities, respectively. A proximal end 606 of the catheter 600 is configured to connect to an external delivery device, and can contain a magnet or any other suitable means for docking the catheter 600 to the external delivery device. The proximal end 606, the first branch 602, and the second branch 604 are all in fluid communication such that the therapeutic agent is able to flow from the external delivery device through the proximal end 606 and out through the perforations in the first and second branches 602, 604 of the catheter 600. One such way to provide this fluid communication between the proximal end 606, the first branch 602, and the second branch 604, is to include an interconnected system of lumens extending through each of the proximal end 606, the first branch 602, and the second branch 604.

As illustrated in FIG. 11A the catheter 600 can be formed from a medical grade silicone with a hardness of approximately 55 D. Any other biocompatible material that is known to or conceivable by one of skill in the art could also be used. The catheter 600 can have an outer diameter of approximately 0.075 inches and an inner lumen diameter of approximately 0.050 inches. However, any other suitable dimensions could be used, especially to take into account patient size and age.

As illustrated in FIG. 11B, the proximal end 606 of the catheter 600 is configured to be covert and resides high enough in the nasal cavity to remain hidden. Additionally, the catheter 600 is configured to be positioned away from the septum of the patient, such that it cannot be felt. The catheter 600 is held in place using a curled geometry on a distal end 608 of the second branch 604. FIG. 11C illustrates a perspective view of an external delivery device 610 according to an embodiment of the present invention. The drug reservoir 612 includes a tube 614 having magnetic coupling configured to dock the external delivery device 610 to the catheter 600. The tube 614 is configured to extend far enough into the nasal passage such that it can dock with the catheter 600.

Figure 12:
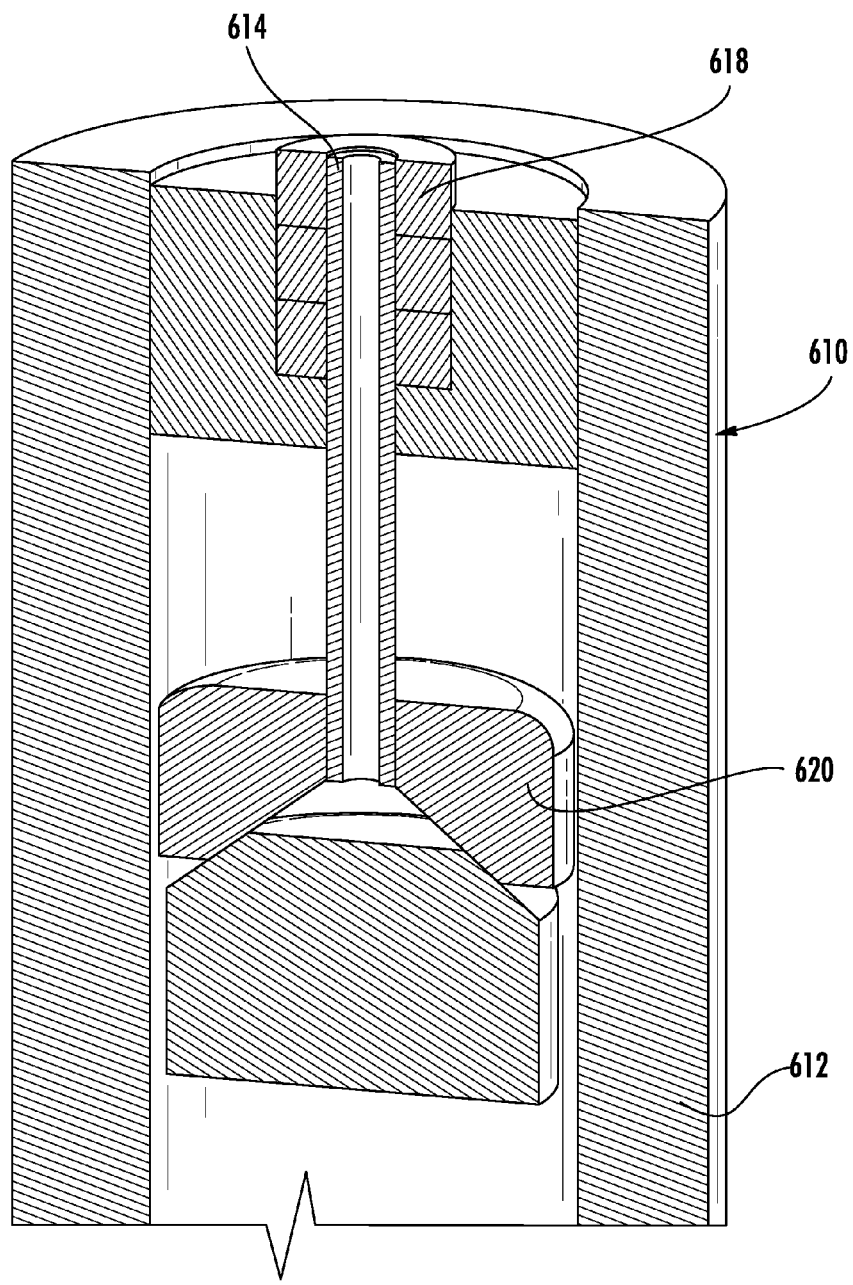
FIG. 12 illustrates a sectional view of the external delivery device of FIG. 11C, according to an embodiment of the present invention.

FIG. 12 illustrates a sectional view of the external delivery device of FIG. 11C, according to an embodiment of the present invention. The external device 610 is composed of a rigid top and a squeezable bottom. When the squeezable bottom is squeezed by the patient, pressurization of the fluid will cause it to travel up the bottle through the interface 616 between the bottle and the catheter and into the catheter. The rigid top of the bottle holds a soft tube that houses a magnet 618 for locating to the inserted catheter. It also houses the button that the patient when the irrigation is complete in order to disengage the external device from the inserted catheter.

The interface between the external device and the inserted catheter is designed so the patient can blindly connect the two components. The patient will insert the soft tube portion of the external device through the opening of the nostril until the two devices connect. The proximal end of the indwelling catheter and the distal end of the external device contain ring magnets that will attract each other to facilitate a connection when in close proximity. The two magnets have the same inner diameter so the saline is smoothly delivered across the connection. The magnets will be titanium-coated for biocompatibility, made of a magnetic ferrous material, and will have a 0.050 inch inner diameter.

The interface between inserted catheter and the external device is further enhanced by an anti-leak mechanism. FIG. 12 further illustrates the function of this anti-leak feature. Fluid pressure compresses the coupling neck spring and moves the coupling neck 620 out past the magnets of the external device, which creates a continuous leak-proof tunnel between the external and inserted portions.

Figure 13:
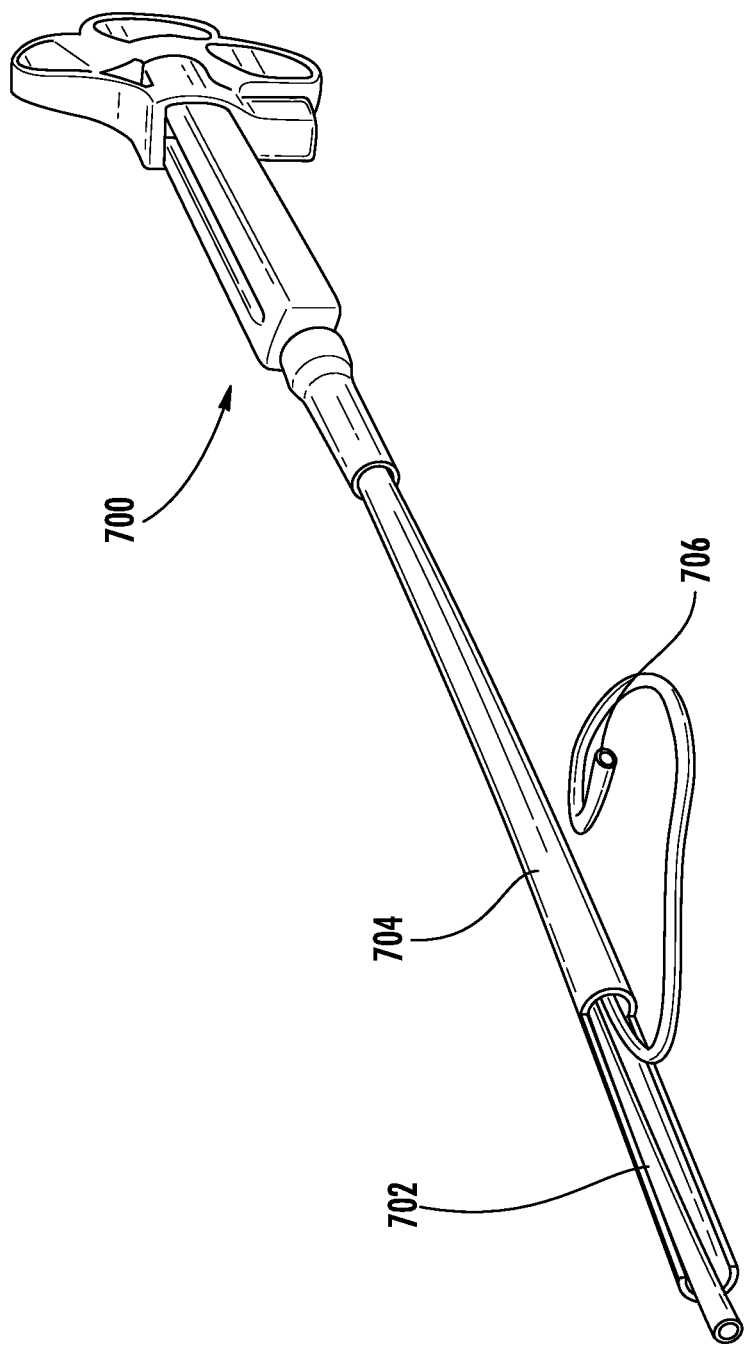
FIG. 13 illustrates a delivery device according to an embodiment of the present invention.

FIG. 13 illustrates a delivery device 700 according to an embodiment of the present invention. The catheter 702 is inserted using a sheath 704 which maintains the catheter in a collapsed state, allowing the physician to maneuver it into position without damaging the surrounding tissue. The catheter 702 can be removed by re-sheathing it in the physician's office. Device placement requires the use of a delivery sheath 704 for placement. Prior to placement, the delivery sheath 704 covers the device and encompasses the distal end 706 forcing the catheter 702 to take the shape of the delivery sheath 704. During placement, the delivery sheath 704 is removed, which allows the distal end 706 of the device 702 to unfurl within the maxillary sinus cavity. For removal, another sheath can be pushed over the outer diameter of the device to straighten the catheter, enabling the physicians to pull out the device without any damage to the surrounding tissue. The delivery sheath will be thin and stiff medical grade silicone tubing in order to facilitate maneuverability during use. It will have a diameter of approximately 0.2 inches.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for delivery of a therapeutic substance to a user's sinus cavity comprising:
    an implantable tube having a proximal end, a distal end, and a lumen extending therethrough, wherein the implantable tube is configured to extend into the user's sinus cavity via the user's nasal passage, and wherein the implantable tube is configured to transmit the therapeutic substance to the user's sinus cavity;
    an anchor segment coupled to the implantable tube configured to secure the implantable tube in the sinus cavity;
    a delivery tube configured to extend into the user's nasal passage;
    an external delivery component having a reservoir coupled to the delivery tube configured to extend into the user's nasal passage, wherein the external delivery component is configured to deliver the therapeutic substance through the delivery tube and into the implantable tube for delivery into the user's sinus cavity; and
    an interface between the implantable tube and the delivery tube coupled to the external delivery component configured to guide and lock the implantable tube to the delivery tube coupled to the external delivery component, wherein the interface between the implantable tube and the delivery tube coupled to the external delivery component is disposed within the user's nasal passage.

2. The system for delivery of the therapeutic substance to the user's sinus cavity of claim 1, wherein the interface comprises a magnetic interface.

3. The system for delivery of the therapeutic substance to the user's sinus cavity of claim 1, wherein the anchor segment further comprises a curved configuration for securing the implantable tube within a maxillary sinus cavity of the user.

4. The system for delivery of the therapeutic substance to a user's sinus cavity of claim 1, wherein the anchor segment comprises a shape memory wire.

5. The system for delivery of the therapeutic substance to a user's sinus cavity of claim 1 further comprising the implantable tube being disposed in an ethmoidal sinus of the user.

6. The system for delivery of the therapeutic substance to the user's sinus cavity of claim 1 further comprising a delivery sheath configured to deliver the implantable tube to the user's sinus cavity, wherein the delivery sheath is further configured to compress the anchor segment until the implantable tube is in a desired location in the user's sinus cavity.

7. The system for delivery of the therapeutic substance to the user's sinus cavity of claim 1, wherein the implantable tube further comprises perforations to allow the therapeutic substance to transmit into the user's sinus cavity.

8. The system for delivery of the therapeutic substance to the user's sinus cavity of claim 1, wherein the lumen of the implantable tube is in fluid communication with a lumen of the delivery tube.

9. The system for delivery of the therapeutic substance to the user's sinus cavity of claim 1, wherein the external delivery component comprises a mechanism configured to apply force to separate the interface between the external delivery device and the implantable tube.

* * * * *